(12) United States Patent
Hartle et al.

(10) Patent No.: US 7,168,205 B2
(45) Date of Patent: Jan. 30, 2007

(54) SEED COAT FOR MANUFACTURED SEEDS

(75) Inventors: Jeffrey E. Hartle, Tacoma, WA (US);
Mollie K. Heilesen, Tacoma, WA (US);
William C. Carlson, Olympia, WA (US)

(73) Assignee: Weyerhaeuser Co., Federal Way, WA (US)

( * ) Notice: Subject to any disclaimer, the term of this patent is extended or adjusted under 35 U.S.C. 154(b) by 0 days.

(21) Appl. No.: 10/011,540

(22) Filed: Dec. 5, 2001

(65) Prior Publication Data

US 2003/0101643 A1   Jun. 5, 2003

(51) Int. Cl.
*A01C 1/06* (2006.01)
(52) U.S. Cl. ............. 47/57.6; 47/DIG. 9; 47/DIG. 11; 504/100
(58) Field of Classification Search ................ 47/57.6, 47/DIG. 9, DIG. 11, 1.01 R; 504/100
See application file for complete search history.

(56) References Cited

U.S. PATENT DOCUMENTS

| | | |
|---|---|---|
| 2,502,809 A | 4/1950 | Vogelsang |
| 3,545,129 A | 12/1970 | Schreiber et al. |
| 3,688,437 A | 9/1972 | Hamrin |
| 3,734,987 A | 5/1973 | Hamrin |
| 3,850,753 A | 11/1974 | Chibata et al. |
| 4,166,006 A | 8/1979 | Hertl et al. |
| 4,252,827 A | 2/1981 | Yokoyama et al. |
| 4,465,017 A | 8/1984 | Simmons |
| 4,562,663 A | 1/1986 | Redenbaugh |
| 4,583,320 A | 4/1986 | Redenbaugh |
| 4,615,141 A | 10/1986 | Janick et al. |
| 4,665,648 A | 5/1987 | Branco et al. |
| 4,715,143 A | 12/1987 | Redenbaugh et al. |
| 4,769,945 A | 9/1988 | Motoyama et al. |
| 4,777,762 A | 10/1988 | Redenbaugh et al. |
| 4,779,376 A | 10/1988 | Redenbaugh |
| 4,780,987 A | 11/1988 | Nelson et al. |

(Continued)

FOREIGN PATENT DOCUMENTS

CA      1241552     9/1988

(Continued)

OTHER PUBLICATIONS

WWW.OBIO.Com, Oppenheimer Biotechnology, Inc. Hydrocarbons; http://www.obio/hydrocarbon%20chains.htm; 2 pages [retrieved from the internet on Aug. 27, 2002].*

(Continued)

*Primary Examiner*—Andrea M. Valenti
(74) *Attorney, Agent, or Firm*—Christensen O'Connor Johnson Kindness

(57) ABSTRACT

The present invention relates to an improved coating for manufactured seeds wherein the coating is able to resist cracking at temperatures below about 1° C. The coating usable with the present invention is comprised of a wax impregnated cellulose substrate wherein the wax composition is comprised substantially of paraffin hydrocarbon cellulose substrata having a Gaussian distribution of carbon chain length ranging from 21 carbons per chain to 40 carbons per chain and a maximum number of paraffin hydrocarbon chains having 31 carbons per chain. One aspect of the present invention is that it provides a wax formulation able to resist cracking at low temperatures and also a wax formulation with a desirable viscosity for commercial manufactured seed coat applications.

23 Claims, 6 Drawing Sheets

U.S. PATENT DOCUMENTS

| | | | |
|---|---|---|---|
| 4,802,305 A | 2/1989 | Kojimoto et al. | |
| 4,806,357 A | 2/1989 | Garrett et al. | |
| 4,808,430 A | 2/1989 | Kouno | |
| 4,866,096 A | 9/1989 | Schweighardt | |
| 4,879,839 A | 11/1989 | Gago et al. | |
| 5,010,685 A | 4/1991 | Sakamoto et al. | |
| 5,044,116 A | 9/1991 | Gago et al. | |
| 5,236,469 A * | 8/1993 | Carlson et al. | 47/57.6 |
| 5,250,082 A | 10/1993 | Teng et al. | |
| 5,258,132 A * | 11/1993 | Kamel et al. | 252/94 |
| 5,284,765 A | 2/1994 | Bryan et al. | |
| 5,427,593 A * | 6/1995 | Carlson et al. | 435/430.1 |
| 5,451,241 A * | 9/1995 | Carlson et al. | 47/57.6 |
| 5,564,224 A * | 10/1996 | Carlson et al. | 47/57.6 |
| 5,666,762 A * | 9/1997 | Carlson et al. | 47/57.6 |
| 5,687,504 A * | 11/1997 | Carlson et al. | 435/430 |
| 5,701,699 A * | 12/1997 | Carlson et al. | 435/420 |
| 5,732,505 A * | 3/1998 | Carlson et al. | 47/57.6 |
| 6,119,395 A * | 9/2000 | Hartle et al. | 47/57.6 |

FOREIGN PATENT DOCUMENTS

| | | |
|---|---|---|
| CA | 1250296 | 2/1989 |
| EP | 0 107 141 A1 | 5/1984 |
| EP | 0 300 730 A1 | 1/1989 |
| EP | 0 380 692 A1 | 8/1990 |
| JP | 61040708 | 2/1986 |
| JP | 62275604 | 11/1987 |
| JP | 63133904 | 6/1988 |
| JP | 63152905 | 6/1988 |
| JP | 2-46240 | 2/1990 |
| JP | 407179683 A * | 7/1995 |
| WO | WO 91/01803 | 2/1991 |

OTHER PUBLICATIONS

Healthy candles.org [retrieved from the internet Nov. 29, 2004] 3 pages.*

Dharma Trading Co., Wax and Waxing Tools, Info section, 2 pages [retrieved from the internet Nov. 29, 2004].*

Smithsonian Physical Tables, Table 121—Densities and Melting and Boiling Points of Organic Compounds, anonymous, undated, 1 page.*

Adlercreutz, P., and B. Mattiasson, "Oxygen Supply to Immobilized Cells: 1. Oxygen Production by Immobilized *Chlorella pyrenoidosa*," *Enzyme Microbial Technol.* 4:332-336, 1982.

Adlercreutz, P., and B. Mattiasson, "Oxygen Supply to Immobilized Biocatalysts. A Model Study," *Acta Chem. Scand. B*36:651-653, 1982.

Adlercreutz, P., and B. Mattiasson, "Oxygen Supply to Immobilized Cells. 3. Oxygen Supply by Hemoglobin or Emulsions of Perfluorochemicals," *Eur. J. Appl. Microbiol. & Biotechnol.* 16:165-170, 1982.

Bapat, V.A., "Studies on Synthetic Seeds of Sandalwood (*Santalum album* L.) and Mulberry (*Morus indica* L.)," in K. Redenbaugh (ed.), *Synseeds: Applications of Synthetic Seeds to Crop Improvement*, CRC Press, Inc., Boca Raton, Fla., 1993, pp. 381-407.

Bapat, V.A., and P.S. Rao, "In Vivo Growth of Encapsulated Axillary Buds of Mulberry (*Morus indica* L.)," *Plant Cell, Tissue and Organ Culture* 20:69-70, 1990.

Bapat, V.A., and P.S. Rao, "Sandalwood Plantlets from 'Synthetic Seeds,'" *Plant Cell Reports* 7:434-436, 1988.

Buchenauer, H., "Mode of Action and Selectivity of Fungicides Which Interfere with Ergosterol Biosynthesis," *Proceedings of the 1977 British Crop Protection Conference—Pests and Diseases*, Brighton, U.K., 1977, pp. 699-711.

Chandler, D., et al., "Effects of Emulsified Perfluorochemicals on Growth and Ultrastructure of Microbial Cells in Culture," *Biotechnol. Letters* 9(3):195-200, 1987.

Clark, Jr., L.C., et al., "Emulsions of Perfluoronated Solvents for Intravascular Gas Transport," *Fed. Proceed.* 34(6):1468-1477, 1975.

Clark, Jr., L.C., et al., "The Physiology of Synthetic Blood," *J. Thorac. & Cardiovasc. Surg.* 60(6):757-773, 1970.

Damiano, D., and S.S. Wang, "Novel Use of a Perfluorocarbon for Supplying Oxygen to Aerobic Submerged Cultures," *Biotechnol. Letters* 7(2):81-86, 1985.

Datta, S.K., and I. Potrykus, "Artificial Seeds in Barley: Encapsulation of Microspore-Derived Embryos," *Theor. Appl. Genet.* 77:820-824, 1989.

Davis, S.S., et al., "Novel Compositions of Emulsified Perfluorocarbons for Biological Applications," *Brit. J. Pharmacol.* 89:665P, 1986.

Dumet, D., et al., "Cryopreservation of Oil Palm (*Elaeis guincesis Jacq.*) Somatic Embryos Involving a Desiccation Step," *Plant Cell Reports* 12:352-355, 1993.

Ebert, W.W., and P.F. Knowles, "Inheritance of Pericarp Types, Sterility, and Dwarfness in Several Safflower Crosses," *Crop Science* 6:579-582, 1966.

Fujii, A., et al., "Artificial Seeds for Plant Propagation," *Trends in Bio/Technol.* 5:335-339, 1987.

Fujii, J., et al., "ABA Maturation and Starch Accumulation in Alfalfa Somatic Embryos" (Abstract), *In Vitro* 25 (3, Part 2):61A, 1989.

Fujii, J., et al., "Improving Plantlet Growth and Vigor From Alfalfa Artificial Seed" (Abstract), *In Vitro* 24 (3, Part 2):70A, 1989.

Fujita, T., et al., "Fluorocarbon Emulsion as a Candidate for Artificial Blood," *Europ. Surg. Res.* 3:436-453, 1971.

Geyer, R.P., "'Bloodless' Rats Through the Use of Artificial Blood Substitutes," *Fed. Proceed* 34(6):1499-1505, 1975.

Gray, D.J., and A. Purohit, "Somatic Embryogenesis and Development of Synthetic Seed Technology," *Crit. Rev. Plant Sci.* 10(1):33-61, 1991.

Grob, J.A., et al., "Dimensional Model of Zygotic Douglas-Fir Embryo Development," *Int. J. Plant Sci.* 160(4):653-662, 1999.

Gupta, P.K., and D.J. Durzan, "Biotechnology of Somatic Polyembryogenesis and Plantlet Regeneration in Loblolly Pine," *Bio/Technol.* 5:147-151, 1987.

Ibarbia, E.A., "Synthetic Seed: Is It the Future," *Western Grower and Shipper* 59:12, 1988.

Janick, J., "Production of Synthetic Seed via Desiccation and Encapsulation" (Abstract), *In Vitro* 24 (3, Part 2):70A, 1989.

Kamada, H., et al., "New Methods for Somatic Embryo Induction and Their Use for Synthetic Seed Production" (Abstract), *In Vitro* 24 (3, Part 2): 71A 1988.

Kim, Y.-H., and J. Janick, "ABA and Polyox-Encapsulation or High Humidity Increases Survival of Desiccated Somatic Embryos of Celery," *HortScience* 24(4):674-676, 1989.

King, A.T., et al., "Perfluorochemicals and Cell Culture," *Biotechnol.* 7:1037-1042, 1989.

Kitto, S.L., and J. Janick, "A Citrus Embryo Assay to Screen Water-Soluble Resins as Synthetic Seed Coats," *HortScience* 20(1):98-100, 1985.

Kitto, S.L., and J. Janick, "Production of Synthetic Seeds by Encapsulating Asexual Embryos of Carrot," *J. Amer. Soc. Hort. Sci.* 110(2):277-282, 1985.

Li, X.-Q., "Somatic Embryogenesis and Synthetic Seed Technology Using Carrot as a Model System," in K. Redenbaugh (ed.), *Synseeds: Applications of Synthetic Seeds to Crop Improvement*, CRC Press, Inc., Boca Raton, Fla., 1993, pp. 289-304.

Mattiasson, B., and P. Adlercreutz, "Use of Perfluorochemicals for Oxygen Supply to Immobilized Cells," *Ann. N.Y. Acad. Sci.* 413:545-547, 1984.

Paulet, F., et al., "Cryopreservation of Apices of *In Vitro* Plantlets of Sugarcane (*Saccharum* sp. Hybrids) Using Encapsulation/Dehydration," *Plant Cell Rep.* 12:525-529, 1993.

Redenbaugh, K., et al., "Encapsulation of Somatic Embryos for Artificial Seed Production" (Abstract), *In Vitro* 20(2):256-257, 1984.

Redenbaugh, K., et al., "Encapsulated Plant Embryos," *Biotechnology in Agriculture*, 1988, pp. 225-248.

Redenbaugh, K., et al., "Encapsulation of Somatic Embryos in Synthetic Seed Coats," *HortScience* 22(5):803-809, 1987.

Redenbaugh, K., et al., "III.3 Artificial Seeds—Encapsulated Somatic Embryos," *Biotech. in Agr. & For.* 17:395-416, 1991.

Redenbaugh, K., et al., "Scale-Up: Artificial Seeds," in Green et al. (eds.), *Plant Tissue and Cell Culture*, Alan R. Liss, Inc., New York, 1987, pp. 473-493.

Redenbaugh, K., et al., "Somatic Seeds: Encapsulation of Asexual Plant Embryos," *Bio/Technology* 4:797-801, 1986.

Riess, J.G., and M. Le Blanc, "Perfluoro Compounds as Blood Substitutes," *Angew. Chem. Int. Ed. Engl.* 17(9):621-634, 1978.

Sanada, M., et al., "Celery and Lettuce," in M.K. Redenbaugh (ed.), *Synseeds: Applications of Synthetic Seeds to Crop Improvement*, CRC Press, Inc., Boca Raton, Fla., 1993, pp. 305-322.

Senaratna, T., "Artificial Seeds," *Biotech Adv.* 10(3)79-392, 1992.

Stuart, D.A., and M.K. Redenbaugh, "Use of Somatic Embryogenesis for the Regeneration of Plants," in H.M. LeBaron et al. (eds.), *Biotechnology in Agricultural Chemistry*, American Chemical Society, Washington, D.C., 1987, pp. 87-96.

Teasdale, R.D., and P.A. Buxton, "Culture of *Pinus radiata* Embryos With Reference to Artificial Seed Production," *New Zealand J. For. Sci.* 16:387-391, 1986.

Tessereau, H. et al., "Cryopreservation of Somatic Embryos: A Tool for Germplasm Storage and Commercial Delivery of Selected Plants," *Ann. Bot.* 74:547-555, 1994.

Timmis, R., "Bioprocessing for Tree Production in the Forest Industry: Conifer Somatic Embryogenesis," *Biotechnology Progress* 14(1):156-166, 1998.

\* cited by examiner

| TEMPERATURE °C | VISCOSITY CENTIPOISE | SHEAR RATE SEC$^{-1}$ |
|---|---|---|
| 74 | 183 | 93 |
| 85 | 134 | 93 |
| 95 | 102 | 93 |
| 104 | 79 | 93 |
| 115 | 62 | 93 |
| 125 | 50 | 93 |
| 135 | 40 | 93 |
| 146 | 32 | 93 |
| 156 | 28 | 93 |
| 165 | 23 | 93 |

NOTES: ANALYSIS PERFORMED WITH BROOKFIELD RVDT WITH THERMOCEL SPINDLE #21. VISCOSITY OF SOME MATERIALS IS DEPENDENT ON SHEAR RATE.

| CARBON | ANALYTE | mg/kg |
|---|---|---|
| C21 | HENEICOSANE | 330 |
| C22 | DOCOSANE | 1800 |
| C23 | TRICOSANE | 5500 |
| C24 | TETRACOSANE | 11000 |
| C25 | PENTACOSANE | 18000 |
| C26 | HEXACOSANE | 24000 |
| C27 | HEPTACOSANE | 37000 |
| C28 | OCTACOSANE | 40000 |
| C29 | NONACOSANE | 43000 |
| C30 | TRIACOTANE | 42000 |
| C31 | HENTRIACONTANE | 44000 |
| C32 | DOTRIACONTANE | 41000 |
| C33 | TRITRIACONTANE | 40000 |
| C34 | TETRATRIACONTANE | 34000 |
| C35 | PENTATRIACONTANE | 28000 |
| C36 | HEXATRACONTANE | 18000 |
| C37 | HEPTATRIACONTANE | 16000 |
| C38 | OCTATRIACONTANE | 12000 |
| C39 | NONATRIACONTANE | 8000 |
| C40 | TERACONTANE | 6500 |
| TOTAL | | 470130 |

*Fig. 4.*

SEED COAT FOR MANUFACTURED SEEDS

FIELD OF THE INVENTION

The present invention relates to manufactured seeds. More particularly, it relates to coatings for manufactured seeds that are able to withstand cracking at low temperatures.

BACKGROUND OF THE INVENTION

Manufactured seed technology allows the mass production of substantially identical plants without the time and labor-intensive exercise of sexual reproduction. Manufactured seed technology has been described in various patents assigned to the Weyerhaeuser Company of Federal Way, Washington, including U.S. Pat. No. 5,236,469, "Oxygenated Analogs of Botanic Seed"; U.S. Pat. No. 5,427,593, "Analogs of Botanic Seed"; U.S. Pat. No. 5,451,241, "Oxygenated Analogs of Botanic Seeds"; U.S. Pat. No. 5,701,699, "Manufactured Seed with Enhanced Pre-Emergence Survivability"; and U.S. Pat. No. 6,119,395, "End Seals for Manufacturing Seed." Plants produced by this technology are genetically tailored to grow optimally in a particular locale and are capable of possessing certain other desirable traits through an in vitro culture of somatic or zygotic plant embryos.

Genetically tailored seeds, when compared to those produced by sexual reproduction, are desirable because sexual reproduction is often subject to genetic recombinational events that may result in variable traits in the progeny. Plant embryos created by in vitro cultures, however, lack the natural protective and nutritive features of natural botanic seeds; thus manufactured seed technology provides both protection and nutrition to plant embryos cultured in a laboratory. Without the protective features afforded by manufactured seeds, in vitro cultures lack shelter from the harsh soil environment and nutrients for survival during the critical stages of sowing and germination.

The coating of a manufactured seed is an important protective feature. Some embodiments of manufactured seeds utilize a seed coat made from wax impregnated paper having a wax component comprised of nine parts paraffin such as that available from Koster Keunen, Inc., Watertown, Conn. (CAS #8002-74-2), and one part carnauba wax, also available from Koster Keunen, Inc. (CAS #8015-86-9) (i.e., a 9:1 ratio of paraffin to carnauba). This wax mixture, when used in connection with a manufactured seed coat, has been observed by the present inventors to crack at temperatures around 1° C. and below. Cracks or microfissures in the manufactured seed coat leave the embryo susceptible to attack by microbes, fungi, and bacteria. Moreover, microfissures or cracks leave the plant embryo susceptible to desiccation and mechanical damage all of which reduce the seed's chances for successful germination.

Microcracking of the manufactured seed coat at lower temperatures poses an even greater challenge to successful germination in light of recently improved methods for long-term storage disclosed in U.S. Pat. No. 5,666,762, "Respiration-Limited Manufactured Seed," and U.S. Pat. No. 5,732,505, "Manufactured Seed Comprising Desiccated and/or Frozen Plant Tissue," also assigned to the Weyerhaeuser Company. These improved methods of long-term storage may require exposing manufactured seeds to temperatures at or below freezing for an extended period of time.

Several wax formulations exist that will resist cracking at temperatures below about 1° C.; however, these waxes do not possess other properties necessary for use with manufactured seeds. For example, manufactured seeds of the kind described herein use a cellulose containing portion, such as a paper straw. The wax composition is applied to the cellulose straw by one of a variety of suitable application processes. Application of the wax composition requires a wax with a viscosity unique to the specific application process utilized. Feasible application processes range from dipping the paper straw within melted wax to spraying the wax thereon. Additionally, manufactured seeds must be able to maintain a degree of rigidity and the wax used with the manufactured seed coat must be able to stay solid (i.e., not melt) under ambient conditions which can be quite hot, especially when the seed is on a slope exposed to direct sunlight. Thus, the wax composition usable with manufactured seeds must possess a melting point and viscosity suitable for use in connection with a manufactured seed coat.

Based on the foregoing, there is a need for an improved seed coat for manufactured seeds having the ability to resist microcracking caused by exposure to cold temperatures. Additionally, there exists a need for a wax formulation for use with manufactured seed coats that has properties consistent with such a use (i.e., an appropriate melting point to resist flow, and an appropriate viscosity for either manual or automated application) and can permit the manufactured seed coat to resist cracking at temperatures below about 1° C.

SUMMARY OF THE INVENTION

With recognition of the problems described above and those which will become more apparent from the detailed description below, the present invention provides manufactured seeds and methods for making manufactured seeds having seed coats comprised of a cellulose substrate and a wax composition wherein the manufactured seed coat is able to resist cracking at temperatures below about 1° C. In a preferred embodiment, the manufactured seed includes a seed coat made from a cellulose substrate and a wax composition with a viscosity of about 23 centipoise to about 50 centipoise at a predetermined application temperature.

In a preferred embodiment, the wax composition comprising part of the seed coat can include about 47% by weight paraffin hydrocarbon chains having 21 to 40 carbons per chain. Additionally, the paraffin hydrocarbon chains included in the wax composition used with the preferred embodiment of the present invention have a Gaussian distribution with a maximum carbon chain length within the range of 28 to 33.

The following detailed description demonstrates that the present invention permits the production of manufactured seeds having seed coats that can resist cracking at temperatures below about 1° C. and exhibit other desirable properties making the invention conducive to application in a variety of manufactured seed uses.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 4 is a table showing the amount of paraffin hydrocarbon in the preferred wax composition useable with the present invention;

DETAILED DESCRIPTION OF PREFERRED EMBODIMENTS

The seed coat for a manufactured seed according to the present invention can be used in conjunction with any manufactured seed design including, but not limited to, those discussed in U.S. Pat. No. 4,769,945, "Delivery Unit of Plant Tissue," assigned to Kirin Brewery Co., Ltd., Tokyo, Japan; U.S. Pat. No. 5,382,269, "Artificial Seeds" assigned to Rhone-Poulenc Agrochimie, Lyons, France; and U.S. Pat. No. 6,164,012, "Biological Material Embedded in Hydrogels, a Process for the Embedding Thereof, and Its Use as Artificial Seed," assigned to Bayer Aktienge-Sellschaft, Leverkusen, Germany, as well as European Patent 0696163B1 and Dupuis et al., *Bio/Technology* 12:385–389, 1994. The seed coat as described herein is used to enclose an embryo comprised of a unit of totipotent plant tissue and a hydrated gel, thereby protecting the embryo from mechanical damage, desiccation, attack by pathogens, herbivores, and other pests.

A. Exemplary Structure for a Manufactured Seed

Figure 1:
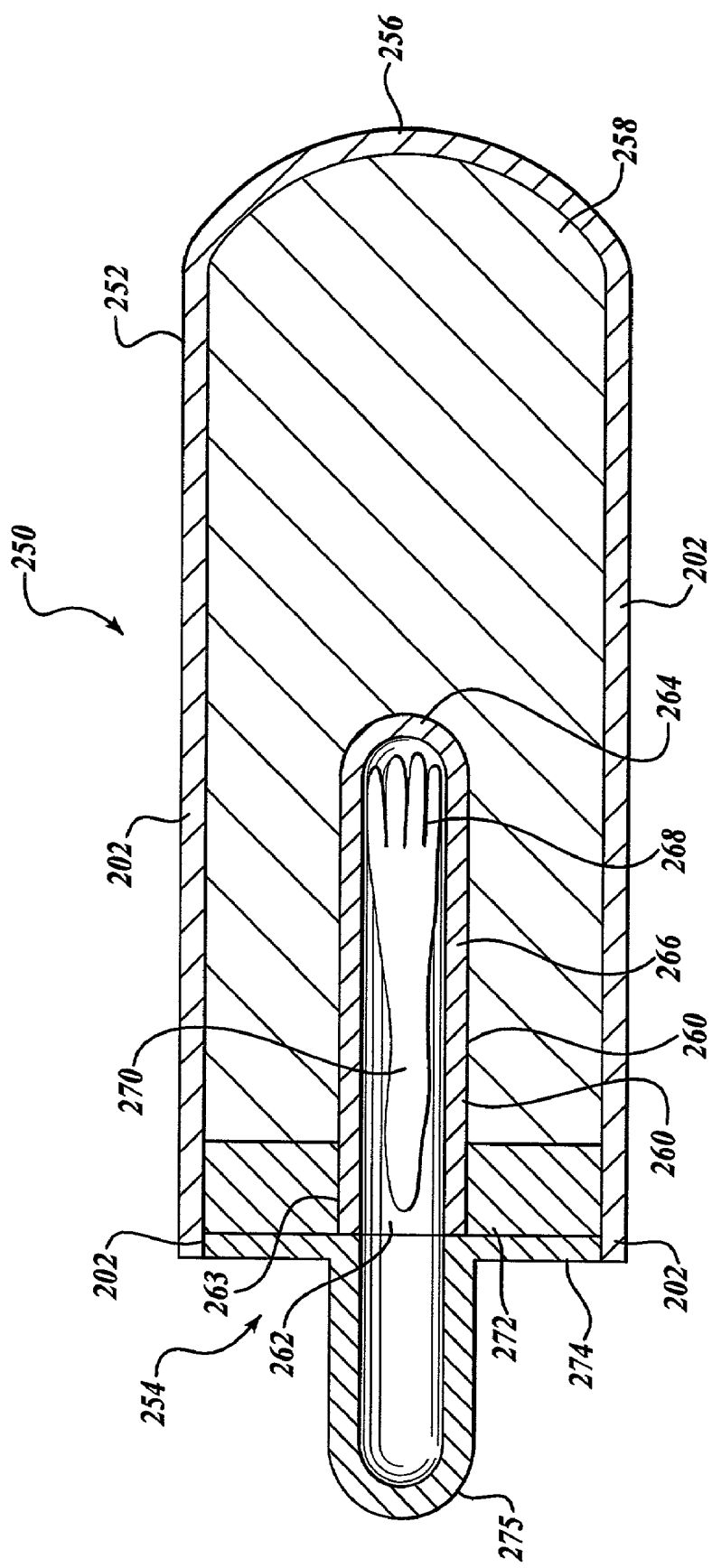
FIG. 1 is a cross-sectional view of a manufactured seed made in accordance with the present invention.

A structural embodiment of a manufactured seed suitable for use with a seed coat according to the present invention is shown in FIG. 1 where the manufactured seed 250 has a lid 274 with a nipple 275 or protruding portion. A manufactured seed of the kind depicted in FIG. 1 is described in greater detail in U.S. Pat. No. 6,119,395 assigned to the Weyerhaeuser Company of Federal Way, Wash., incorporated herein by reference in its entirety. Generally, the manufactured seed 250 comprises a seed coat 252 substantially surrounding a hydrated gel 258 that serves as an artificial gametophyte for a unit of totipotent plant tissue 266. The materials comprising the artificial gametophyte and the unit of totipotent plant tissue are described in greater detail below and are also disclosed in U.S. Pat. Nos. 5,427,593; 5,451,241; and 5,701,699, assigned to the Weyerhaeuser Company and hereby incorporated by reference in their entirety. The seed coat 252 provides physical protection for the interior for the manufactured seed 250 while allowing the germinant that develops from the totipotent plant tissue 266 to escape from the manufactured seed during germination.

The seed coat 252 has an open end 254 and a closed end 256. The seed coat 252 according to at least one embodiment of the present invention, can be constructed from a cellulosic material such as a portion of a common paper soda straw such as those available from the Sweetheart Cup Company, Owings Mills, Md. The paper soda straws are preferably about 6.5 mm in diameter and 10 mm to 20 mm long. In accordance with the present invention, the straws are made substantially water resistant by such means as dipping in a liquid hot wax composition such as that described in greater detail below that is a mixture of paraffin available from Koster Keunen, Inc., Watertown, Conn. (CAS #8002-74-2), and Blue Plasti-Ject Injection Jewelry Wax available from the Kindt Collins Company of Cleveland, Ohio. A seed coat 252 made partially of cellulose or other biodegradable materials is preferred so that nursery beds will not be cluttered with spent seed coats from previous crops, although it is also preferred that the seed coat remain intact at least until emergence of the primary root. The closed end 256 can be created by the use of a suitable plug or barrier, or by crimping to form a somewhat domed shaped or conical end.

The hydrated gel 258 used to make the artificial gametophyte can be any of the types of gels known in the art and can, optionally comprise nutrients and oxygen carriers. A preferred gel 258 is agar-based because agar will gel (i.e., "set" or "cure") spontaneously by lowering the temperature. The hydrated gel 258 should be somewhat firm to prevent seepage of liquid from the gel into the cavity 262 containing the plant tissue. Flooding of the cavity 262 can cause a low percentage of normal germinants.

The size of the seed coat 252 can vary, depending upon the species of plant being propagated. The relative dimensions of seed coat 252 and gel 258 depicted in FIG. 1 is suitable for propagation of totipotent plant tissue of conifers and should not be considered limiting for this or other types of plants.

The plant tissue 256 is contained within an inner tube 260 to provide, at least in part, sufficient shoot restraint. The inner tube 260 has an open end 263 and a closed end 264. The plant tissue 266 is situated within the manufactured seed 250 so as to orient the shoot and/or cotyledons 268 toward the closed end 264 and the latent radicle 270 toward the open end 263. The tube 260 can be made of various materials that are not phytotoxic and that permit adequate access of the totipotent plant tissue 266 to moisture, gasses, and nutrients necessary for germination. The materials are also preferably porous. Materials such as, but not limited to, filter paper, plaster of Paris, ceramics, and reasonably rigid and open-celled foams have all proved satisfactory. A tube made from filter paper or similar material can optionally contain small perforations.

The internal diameter of the tube 260 should be sufficient to allow a somewhat enlarged shoot end 268 of the totipotent plant tissue to be in intimate contact with the walls of the tube 260. The tube 260 allows access of nutrients, gasses and liquids necessary for germination to the plant tissue.

A coaxial internal cavity is formed in the hydrated gel 258 to accept the tube 260. After forming the cavity and inserting the tube 260 therein, the plant tissue 266 can be inserted into the tube 260 shoot end first. Either before or after insertion of the plant tissue 266, the manufactured seed 250 can be gassed with oxygen or other gasses.

A primary end seal 272 is applied over the gel surface and around the protruding open end 263 of the tube 260 before insertion of the plant tissue into the gel. However, the primary end seal 272 should not cover the open end 263 of the tube 260. It should be noted that a primary end seal is not necessary and may be omitted. Many materials are suitable for the primary end seal 272. Paraffin wax of the kind described thus far has proved suitable. A secondary end seal, or lid, 274 is applied so as to cover the open end 263 of the primary end seal 272. As shown in FIG. 1, the lid preferably includes a nipple 275 that extends outwardly from the manufactured seed. Alternatively, however, the lid may be flat and formed either by a prestretched or unstretched material.

The lid 274 is preferably very thin, most typically no more than about 1 mm thick. It can be made of the same material as the primary end seal 272. Preferably, however, the lid 274 is a gas permeable, water impermeable membrane such as prestretched Parafilm®, which can be sealed in place across the open end 263 by heat annealing or mechanical pressure. Stretching a material such as Parafilm® to produce a lid 274 having a protruding portion, or nipple 275, as shown will cause a thinning of the lid in the prestretched region relative to the unstretched portion of the lid. The protruding portion can have any shape or configuration and may be symmetrical or asymmetrical in shape.

As with the seed coat 252, an antibiotic can optionally be added to the outside or the inside of the primary and secondary end seals.

The closed end 264 on the tube 260 has been found to be advantageous. The closed end 264 prevents the shoot end or cotyledons 268 growing inside the tube 260 from penetrating the tube and expanding into the gel 258. Expansion of the shoot end or cotyledons 268 into the gel 258 would result in entrapment in the gel, preventing the growing plant from escaping from the manufactured seed and/or causing germinant abnormalities. The growing shoot end is preferably only temporarily restrained within the tube 260. As it grows and elongates, the shoot end bears against the internal surfaces of the tube; this urges the shoot end out of the tube and, consequently, out of the hydrated gel, simulating the function of a natural seed.

B. Manufactured Seed Coat

With continuing reference to FIG. 1, the manufactured seed coat 252 will be described in greater detail. The manufactured seed coat 252, like a natural seed coat, protects the totipotent plant tissue 266 and other internal structures of the manufactured seed from mechanical damage, desiccation, attack by microbes, fungi, insects, nematodes, birds, and other pathogens, herbivores, and pests, among other functions.

The manufactured seed coat 252 of the present invention can be fabricated from cellulosic materials and waxes. The materials from which the seed coat 252 is made are substantially non-toxic and preferably provide a degree of rigidity. It is preferable that the seed coat 252 be biodegradable, although it is also preferable that the seed coat 252 remain intact until after emergence of the germinating totipotent plant tissue 266. It is also preferable that until after emergence, the seed coat 252 be resistant to penetration by microbial or other plant pathogens. As explained in greater detail below, the manufactured seed coat 252 can resist cracking at temperatures below about 1° C.

The manufactured seed coat 252 includes a containing portion 202 defined on either side by closed end 256 and open end 254. Open end 254 is covered or otherwise occluded by a primary and secondary end seal, 272 and 274, respectively. Alternatively, in place of the primary and secondary end seals, the containing portion can include a region that is thin or weakened relative to other regions of the containing portion. The thinner or weakened portion covers the open end 254 and has a lower burst strength than the rest of the containing portion 202. Thus, a germinating embryo preferentially emerges from the manufactured seed coat by penetrating through the opening or thinner or weaker area of the containing portion 202.

The containing portion 202 is preferably sufficiently rigid to provide mechanical protection to the embryo, e.g., during sowing and is substantially impermeable to gasses, water, and soil microbes. It is preferable that the radicle 268 of the totipotent plant tissue 266 be oriented toward the opening 274 or weaker area of the containing portion 202 to facilitate protrusive growth of the primary root of the germinating totipotent plant tissue 266 from the manufactured seed.

The manufactured seed coat 252 is preferably comprised of two compositions. The first is a cellulose material that is relatively compliant and water permeable. The second composition is a wax that is applied to the cellulose to substantially reduce the water permeability and provide structural rigidity. Reducing water permeability is desirable for at least two reasons. First, water permitted to enter the manufactured seed can dilute nutrients. Second, water permitted to enter the manufactured seed can carry with it microbes and bacteria, among other pests. In one embodiment, the cellulose composition can comprise a relatively compliant cellulosic or analogous material, shaped to at least partially conform to the shape of the mass of the hydrogenated gel to be disposed therein, and having at least one tapered end. For example, in a preferred embodiment, the compliant cellulosic material is a crimped or otherwise tapered paper straw covered by a primary and secondary end seal that may include a nipple 275, as illustrated in FIG. 1.

C. Suitable Wax Formulations

As explained above, the seed coat 252 is preferably comprised of two or more compositions, the first being comprised of cellulosic materials and the second being comprised of a wax composition. The wax composition used to make seed coat 252 is comprised substantially of paraffin wax which is a colorless or white, somewhat translucent, hard wax consisting of a mixture of solid straight chain hydrocarbons ranging in melting point from about 48° to 66° C.

As used herein, the term "paraffin hydrocarbon" is any of the saturated hydrocarbons having the general formula $C_nH_{2n+2}$, C being a carbon atom, H a hydrogen atom, and n an integer. Paraffins containing fewer than 5 carbon atoms per molecule are usually gaseous at room temperature, those having 5 to 15 carbon atoms are usually liquids, and the straight-chained paraffins having more than 15 carbon atoms per molecule are solids. Paraffin hydrocarbons are immiscible with water but are soluble in absolute alcohol, ether, and acetone.

A preferred wax composition usable with the present invention is a 7:3 mixture of Blue Plasti-Ject Injection wax available from the Kindt Collins Company, Cleveland, Ohio, and paraffin wax available from Koster Keunen, Inc. (CAS #8002-74-2). This mixture differs from the wax mixture used with manufactured seed coats of the prior art which typically are a 9:1 mixture of paraffin from Koster Keunen, Inc. (CAS #8002-74-2), and carnauba from Koster Keunen, Inc. (CAS #8015-86-9). The present inventors observed that seed coats made from the prior art wax mixture cracked at temperatures below about 1° C. A preferred wax composition of the present invention is a mixture of 7 parts Blue Plasti-Ject Injection wax and 3 parts paraffin. Other suitable ratios include 6:4, 5:5, 4:5, 4:6, 3:7, 2:8, 1:9, 8:2, and 9:1. While the described wax compositions are preferred, any wax composition having desirable properties for use with a manufactured seed and able to resist cracking at temperatures below about 1° C. can be useful in the present invention. The specific wax compositions described herein are just some examples of suitable wax compositions. As mentioned previously, the wax composition usable with the present invention has a viscosity and melting point conducive for use with manufactured seeds having a cellulose substrate such as a paper straw. The desired viscosity of a suitable wax composition will change depending on the process used for applying the wax composition to the cellulose substrate. A preferred mode of application described herein is dipping the cellulose substrate into a melted wax composition when that wax composition is fluid at a temperature of about 145° C. When this application method is employed, the wax composition should not be so viscous at the application temperature that it is unable to coat all surfaces of the cellulose substrate in a reasonable amount of time or be too thick in places such that there is no uniformity in thickness. On the other hand, the wax composition should not be so flowable at the application temperature that the layer of deposited wax is too thin. Different viscosities will be desirable for different application processes such as spraying or brushing.

Figures 2, 3:
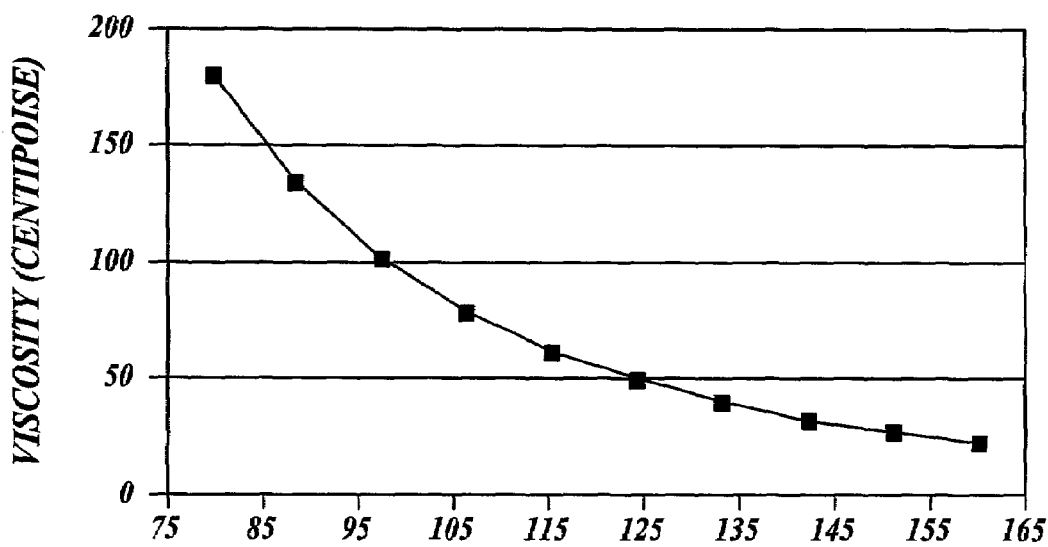
FIG. 2 is a table showing viscosity values in centipoise for a preferred wax useable in accordance with the present invention.
FIG. 3 is a graphical representation of the data depicted in FIG. 2.

Referring now to FIGS. 2 and 3, viscosity tables and graphs explaining the viscosity of a preferred wax composition usable with the present invention are illustrated. FIG. 2 is a table showing the viscosity values in centipoise of a preferred wax composition, where the viscosity is measured by a Brookfield thermocell Spindell #21 at different temperatures. FIG. 2 shows that the viscosity of a preferred wax composition is 23 to 50 centipoise at various temperatures. A wax composition having a viscosity within the range of 23 to 50 centipoise is suitable for many application processes ranging from manual dipping to automated spraying. It is important to note, however, that the present invention is by no means limited to a wax composition having a viscosity within this range. With reference now to FIG. 3, a graphical representation of the data contained in FIG. 2 is depicted. As shown, the viscosity of a preferred wax composition useable with the present invention is 183 centipoise at 74° C. and decreases at a higher rate from 70° C. to 80° C. and then tapers quite gradually until about 165° C. where the viscosity is 23 centipoise.

Figure 5:
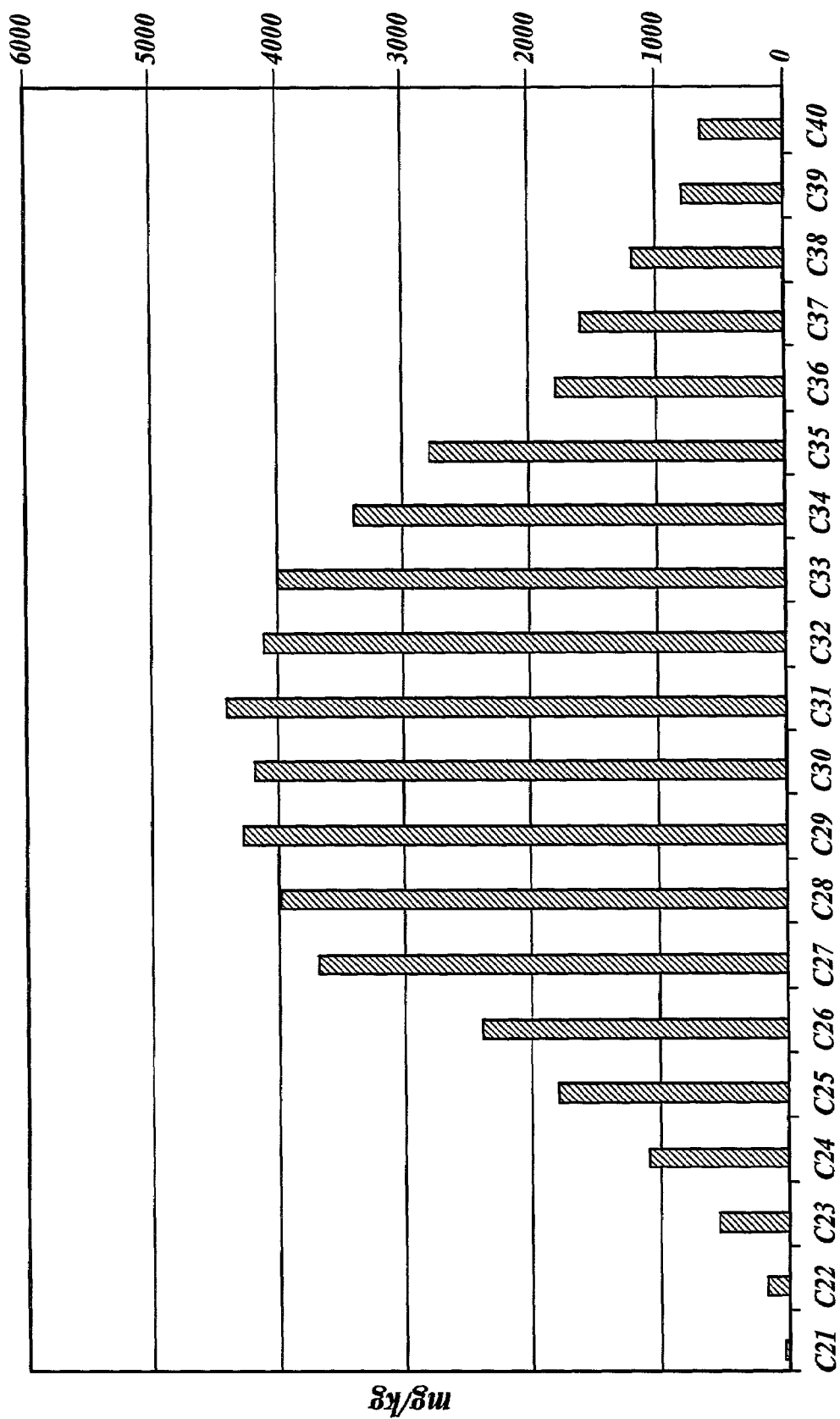
FIG. 5 is a graphical representation of the data contained in FIG. 4.

Referring now to FIGS. 4 and 5, the portion of a preferred wax composition comprising paraffin hydrocarbon is analyzed in greater detail. In a preferred composition the wax composition usable with the present invention has a major paraffin component where the paraffin hydrocarbons range in carbon chain length from C21 to C40. As depicted in FIGS. 4 and 5, a preferred wax composition useable with the present invention comprises about 47% by weight paraffin hydrocarbon having carbon chain lengths ranging from C21–C40. As depicted best in FIG. 5, the distribution of paraffin hydrocarbon in a preferred wax composition is a Gaussian distribution and the maximum type of paraffin hydrocarbon contained within a preferred wax composition is hentriacontane which is a straight chain paraffin hydrocarbon having 31 carbons per chain. Although the specific wax composition depicted in FIGS. 4 and 5 has a maximum paraffin hydrocarbon content comprising hentriacontane it is important to note that a suitable wax composition need not have this as its maximum.

Blue Plasti-Ject Injection wax from the Kindt Collins Company, Cleveland, Ohio, described above, is comprised of about 50% petroleum wax (which is mostly solid paraffin hydrocarbon having at least 15 carbons per chain), about 20% microcrystalline petroleum wax, about 20% ethylene vinyl acetate copolymer and about 10% hydrocarbon resin. This Blue Plasti-Ject Injection wax is normally used in the jewelry industry and by itself, has properties that require it to be heated to such a high temperature to flow at a usable viscosity that it is incompatible with the preparation of seed coats using a cellulose substrate because the cellulose may degrade at such high temperatures. In contrast, paraffin wax available from Koster Keunen, Inc. (CAS #8002-74-2), has viscosity properties that make it too fluid for use in the preparation of seed coats using a cellulose substrate because the layer of wax will be too thin. Moreover, the Koster Keunen paraffin has a melting point that is too low for use with manufactured seed coats because it will flow or melt at many ambient temperatures experienced by seeds in a nursery or in the field, especially those on slopes exposed to intense sunlight. Manufactured seeds must be able to stay solid and protect the plant embryo, thus the coat must be able to stay solid at temperatures of about 49° C. and above.

Accordingly, in accordance with the present invention, a wax composition can be prepared by tailoring a wax that exhibits the desired viscosity properties depending upon the application method. Thus, while a specific embodiment of the present invention has been described above with respect to a 7:3 mixture of Blue Plasti-Ject Injection wax to paraffin, other ratios may provide suitable wax compositions provided that they result in a seed coat that does not crack at temperatures around 1° C. or below. In addition, wax compositions comprising waxes other than paraffin available from Koster Keunen (CAS #8002-74-2), or Blue Plasti-Ject injection wax may be suitable for manufacturing seed coats in accordance with the present invention, provided such wax compositions result in a seed coat that does not crack at around 1° C. or below and exhibit viscosity properties which make the wax composition suitable for application to a cellulose substrate.

D. Suitable Totipotent Plant Tissues

A manufactured seed, according to one aspect of the present invention, comprises a unit of totipotent plant tissue. As is generally known in the art, totipotent plant tissue is obtainable from any of several areas of a plant such as meristematic tissue and plant embryonic tissue.

Meristematic tissue is comprised of undifferentiated plant cells that divide to yield other meristematic cells, as well as differentiated cells that elongate and further specialize to form structural tissues and organs of the plant. Meristematic tissue is located, for example, at the extreme tips of growing shoots or roots, in buds, and in the cambium layer of woody plants.

Plant embryonic tissue can be found (in the form of a "zygotic" embryo) inside a botanic seed of the plant produced by sexual reproduction. Also, plant "somatic" embryos can be produced by culturing totipotent plant tissue such as meristematic tissue by standard methods under laboratory conditions in which the cells comprising the tissue are separated from one another and urged to develop into minute complete embryos. Alternatively, a process termed "cleavage polyembryogeny" known in the art can be induced during natural embryo development in seed.

As used herein, a "unit" of totipotent plant tissue is a mass of such tissue that can be individually handled and that can develop into a germinant and ultimately a plant under favorable conditions.

For use in preferred embodiments of manufactured seeds according to the present invention, the unit of totipotent plant tissue preferably is developed sufficiently to have a shoot end and a radicle end. In certain species of plants, the shoot end includes one or more cotyledons in some stage of development. For example, such totipotent plant tissue of gymnosperms usually has multiple cotyledons situated on or near the shoot apex. This is also the case with many dicotyledonous plants.

Manufactured seeds according to the present invention can include a unit of totipotent plant tissue from any plant species (*dicotyledonous, monocotyledonous, gymnosperm*, etc.).

E. A Suitable Artificial Gametophtye

In manufactured seeds according to the present invention, a hydrated gel, along with any other substances included therein, can serve as an artificial gametophyte for the unit of totipotent plant tissue. The preparation of hydrated gels is well known in the art and it involves conversion of a substance prepared in an aqueous colloidal solution into a semisolid material. (As used herein, "hydrate" denotes the presence of free water interspersed throughout the matrix of gel molecules and "curing" or "setting" of the hydrated gel refers to the process of converting the liquid gel solution into a semisolid material.)

Suitable gel solutes are soluble in water, not cytotoxic and substantially non-phytotoxic. As used herein, a "substantially non-phytotoxic" substance is a substance that does not interfere substantially with normal plant development, such as by killing a substantial number of plant cells, substantially altering cellular differentiation or maturation, causing mutations, disrupting a substantial number of cell membranes or substantially disrupting cellular metabolism, or substantially disrupting some other vital process. Candidate gel solids and the methods of dissolving the solids and preparing the hydrated gel are well known in the art. Specifically, candidate gel solids and the methods for making hydrated gels suitable for use with the present invention are set forth in greater detail in U.S. Pat. No. 6,199,395, incorporated herein by reference in its entirety.

A hydrated gel as discussed above, can be "oxygenated" to have a higher oxygen concentration than what would otherwise be absorbed from the atmosphere. The gel can also be made to include other desirable gases besides oxygen. An oxygenated gel will ensure that the totipotent plant tissue is provided with sufficient oxygen to undergo germination. Oxygenation of a gel or the inclusion of other desirable gases within the gel can be achieved by any of several representative methods, as disclosed extensively in, for example, U.S. Pat. Nos. 5,236,469 and 5,427,593, both incorporated herein by reference in their entirety. Simple germination experiments involving a series of otherwise identical manufactured seeds each of which having a stepwise different oxygen concentration from all other manufactured seeds in the series, can be used to determine the minimum oxygen concentration. Oxygen concentration should be at least adequate to support sufficient growth and germination of the radicle of a particular plant species.

It is preferable to provide the totipotent plant tissue with any of various additives, e.g., plant nutrients and other beneficial substances such as vitamins and a source of carbon and energy (herein collectively termed generally "nutrients"), antibiotics or plant growth regulators. See, e.g., the "adjuvants" listed in U.S. Pat. No. 4,779,376, incorporated herein by reference in its entirety.

The various ways of dispersing such additives into a hydrated gel are well known in the art. A number of appropriate nutrient formulations exist in the art, including a number of proprietary formulations. For example, a popular medium is the "MS liquid" (Murashige and Skoog, *Physiologia Plantarum* 15:473–497(1962)). The nutrient solution can also include plant growth hormones and other compounds serving to further increase the probability of germinant survival.

After preparing the gel liquid, preparing units of cured hydrated gel for use in making manufactured seeds can be done in a number of ways. Fluid transfer between the totipotent plant tissue and the hydrated gel can be accomplished, e.g., by direct contact or via an intervening water permeable "bridge," such as a filter paper. Preferably, the totipotent plant tissue is disposed in a pre-formed hole or cavity in a block of hydrated gel. As discussed above, the preformed hole or cavity preferably includes a shoot restraint. The gel can be cured preformed into a preferred shape or can be formed as a larger cured mass and cut to size and shape as desired before inserting the totipotent plant tissue.

F. Definitions

The following terms as used herein are defined as follows:

"Somatic embryo" is a plant embryo that develops via the laboratory culturing of totipotent plant cells or by induced cleavage polyembryogeny.

"Zygotic embryo" is a plant embryo removed from a seed of the corresponding plant.

"Germinant" is a unit of totipotent plant tissue that has undergone sufficient growth and development to emerge from a seed coat, analogous to emergence from a natural botanic seed.

"Radicle end" is the part of a unit of totipotent plant tissue that develops into the primary root of the plant.

"Shoot" or "shoot end" is that part of a unit of totipotent plant tissue that develops into the aerial portions of the plant and includes the cotyledon(s), epicotyl, and/or hypocotyl.

"Cotyledon" refers generally to the first, first pair, or first whorl (depending on the plant type) of leaf-like structures on a plant embryo that function primarily to make food compounds in the seed available to the developing totipotent plant tissue, but in some cases act as food storage or photosynthetic structures.

"Hypocotyl" is that portion of a plant embryo or seedling located below the cotyledons but above the radicle.

"Epicotyl" is that portion of the plant developed after germination from the stem apex.

"Hypocotyl germinant" denotes the emergence of a shoot from the capsule, caused by elongation of the hypocotyl sufficiently to burst the capsule. This term does not take into consideration any length, criteria or lack of hypocotyl malformations.

"Totipotent" refers to a capacity to grow and develop into a normal plant. Totipotent plant tissue has both the complete genetic information of a plant and the ready capacity to develop into a complete plant if cultured under favorable conditions.

"Artificial Gametophyte" refers to the hydrated gel along with any other substances included therein, to serve as a nutrient source for the totipotent plant tissue.

The invention will be further understood by reference to the following example which is intended to merely illustrate the best mode known for practicing the invention. The scope of the invention is not to be considered limiting thereto however.

EXAMPLE

Paper straws were cut to seed coat forming lengths of 1.9 cm. Once cut, the seed coat length segments were formed into seed coats by crimping one end of the open ends closed. Various wax formulations were prepared by heating the wax in a fume hood to a temperature of 165° C. to 180° C. Twenty-five 1.9 cm segments were dropped into the wax, stirred with a stir bar, and submerged (if needed). Sinking the segments in the wax assures complete inside coating. This took about 2–5 minutes to complete. Once complete, the seed coats were removed one at a time and drained on the lip of a beaker. The open end was then blotted on a stack of Kimwipes® (3–4 high). Once blotted, seed coats were placed over a peg on a drying rack. Seed coats were blotted to prevent wax build up around the open end during drying on the rack. Air drying was used.

Figure 6:
FIG. 6 is a photograph of the seed coat used with manufactured seeds of the prior art magnified 6× after exposure to temperatures below about 1° C.
Figure 7:
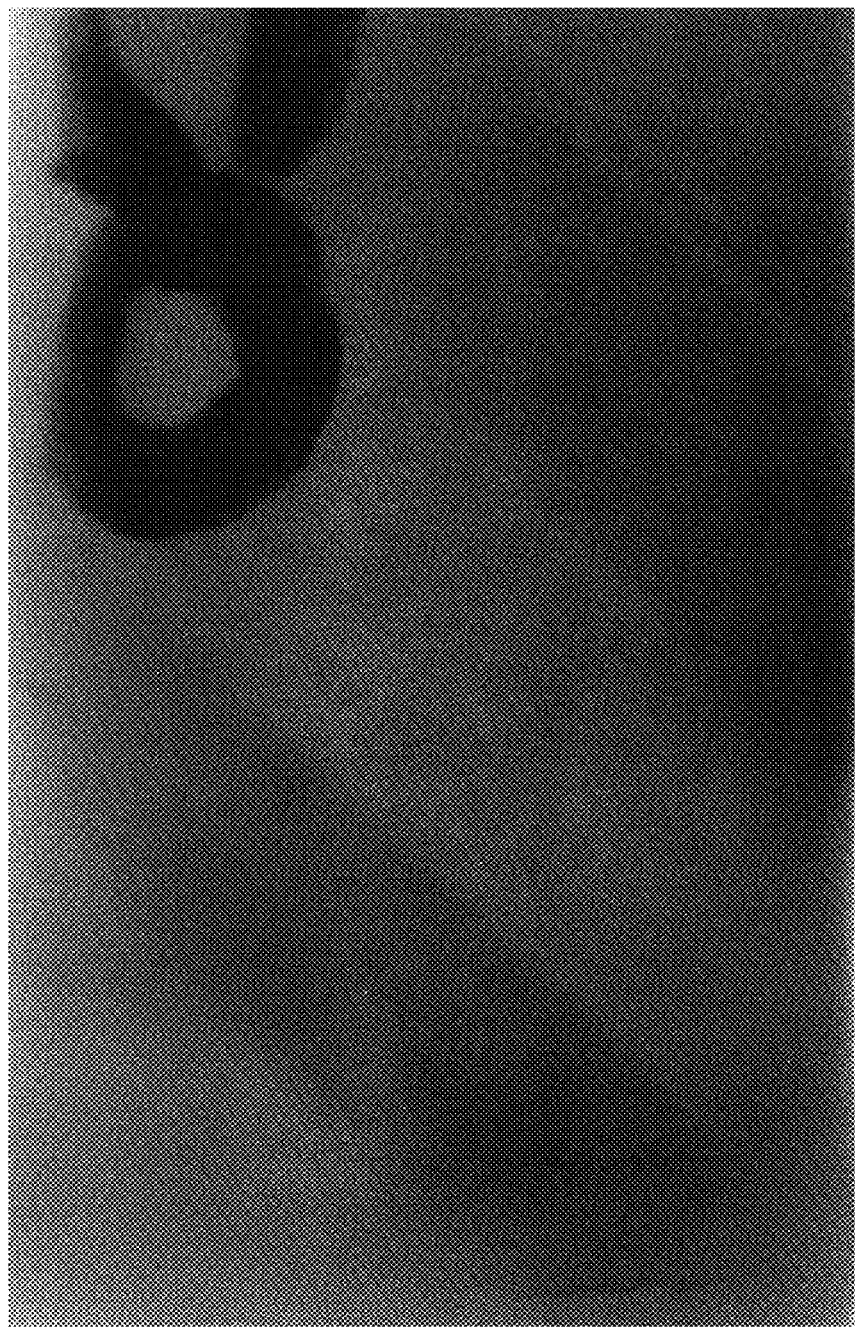
FIG. 7 is a photograph of a seed coat made in accordance with the present invention magnified 6× after exposure to temperatures below about 1° C.

Four separate wax formulations were examined. The first wax formulation is a mixture of paraffin wax available from Koster Keunen, Inc. (CAS #8002-74-2), and carnauba wax also available from Koster Keunen, Inc. (CAS #8015-86-9), at a 9:1 ratio of paraffin to carnauba. This first wax formulation is the wax used in the manufactured seeds described in the prior art. Additional wax formulations were prepared from a mixture of the paraffin wax available from Koster Keunen with Blue Plasti-Ject injection jewelry wax from the Kindt Collins Company, Cleveland, Ohio, in various ratios of Blue Plasti-Ject Injection wax to paraffin. Thirty replicate seed coats were filled, cored and capped for each wax formulation and placed in a 4° C. freezer simultaneously. Daily, throughout a five-day period, the freezer was opened and the seeds were examined for cracks. Cracks were assessed by examining the seeds under a standard dissecting microscope. FIG. 6 shows the seed coat of the prior art and FIG. 7 shows the seed coat made in accordance with the present invention after both were exposed to temperatures of about 1° C. and below. Once the assessment for cracks was done initially, the freezer temperature was lowered by 2° C. until –5° C. was reached. Once the final temperature was reached, the seeds were removed and again assessed for cracks. Results are reported in Table 1.

TABLE 1

| Wax Formulation | Waxed at 180° C. Temperature lowered to 1° C. | Waxed at 180° C. Temperature gradually lowered to +4° C. to –5° C. |
| --- | --- | --- |
| 9:1 paraffin to carnauba mixture (prior art) | All cracked | All cracked |
| 7:3 Blue Plasti-Ject Injection wax to paraffin mixture | No cracks | No cracks |
| 6:4 Blue Plasti-Ject Injection wax to paraffin mixture | No cracks | No cracks |
| 5:5 Blue Plasti-Ject Injection wax to paraffin mixture | No cracks | No cracks |
| 4:5 Blue Plasti-Ject Injection wax to paraffin mixture | No cracks | No cracks |
| 4:6 Blue Plasti-Ject Injection wax to paraffin mixture | No cracks | No cracks |
| 3:7 Blue Plasti-Ject Injection wax to paraffin mixture | No cracks | No cracks |
| 2:8 Blue Plasti-Ject Injection wax to paraffin mixture | No cracks | No cracks |
| 1:9 Blue Plasti-Ject Injection wax to paraffin mixture | No cracks | No cracks |
| 8:2 Blue Plasti-Ject Injection wax to paraffin mixture | No cracks | No cracks |
| 9:1 Blue Plasti-Ject Injection wax to paraffin mixture | No cracks | No cracks |

The data shown above in Table 1 demonstrate that several mixtures of Blue Plasti-Ject Injection wax and Parraffin will not crack at temperatures below about 1° C.

Additionally, seed coats made in accordance with a preferred wax formulation of the present invention were prepared as described above and placed directly into a –20° C. freezer and kept at that temperature for about 24 hours. Following the 24-hour period at –20° C., the seed coat made in accordance with a preferred wax formulation (7:3 mixture of Blue Plasti-Ject Injection wax to paraffin) was assessed for cracks and no cracks were present. The results of this experiment are reported in Table 2.

TABLE 2

| Wax Formulation | Waxed at 145° C. and placed directly into a –28° C. freezer |
| --- | --- |
| 7:3 Blue Plasti-Ject Injection wax paraffin mixture | No cracks |

Biological studies were conducted in nursery soil under a simulated nursery environment to determine the viability of the new seed coat and to determine whether the new wax formulation adversely affects germination. The results of these studies are shown in Tables 3 and 4.

TABLE 3

| | Germination | Normalcy | Lateral Roots | Epicotyl Presence |
| --- | --- | --- | --- | --- |
| Natural Seed | 100% | 100% | 100% | 100% |
| 9:1 paraffin to carnauba mixture (prior art) | 51.4% | 65.7% | 57.1% | 65.7% |
| 7:3 Blue Plasti-Ject Injection wax to paraffin mixture (new wax) | 41.4% | 67.1% | 51.4% | 67.1% |

Table 3 shows the percent germination, normalcy, lateral roots, and epicotyl presence for all treatments. No significant difference was recorded at an α of 0.0005. Germination was scored at 34 days past sowing.

TABLE 4

| | Radical Length | Hypocotyl Length | Cotyledon Length |
| --- | --- | --- | --- |
| 9:1 Paraffin to carnauba mixture (prior art) | 7.94 cm | 2.08 cm | 1.65 cm |
| 7:3 Blue Plasti-Ject Injection wax to paraffin mixture | 6.40 cm | 1.99 cm | 1.60 cm |

Table 4 shows different organ lengths for the prior art wax composition and wax compositions of the present inventors. Table 4 shows generally that the wax formulation of the invention does not result in a statistically significant change in organ length. There were no significant differences at an α of 0.0005 within the data set analyzed. Germination was scored at 34 days past sowing and the values reflect only the normal germinants.

The invention claimed is:

1. A seed coat for manufactured seeds comprising a substrate having a wax coating substantially encasing the substrate and wherein the seed coat resists cracking at temperatures below about 1° C. for at least four days, wherein the wax coating comprises paraffin and a wax composition, wherein a ratio of the wax composition to paraffin is from about 1:9 to about 9:1, and wherein the wax composition comprises about 50% by weight petroleum wax, about 20% by weight microcrystalline petroleum wax, about 20% by weight ethylene-vinyl acetate copolymer, and about 10% hydrocarbon resin.

2. The seed coat of claim 1 wherein said wax coating has a viscosity of about 23 centipoise to about 50 centipoise at a predetermined application temperature.

3. The seed coat of claim 1 wherein said wax coating has a melting point of at least 49° C.

4. The seed coat of claim 1 wherein said substrate is formed from cellulose.

5. The seed coat of claim 1 wherein the paraffin hydrocarbon chains have a Gaussian distribution with a maximum carbon chain length within the range of about 28 to 33.

6. The seed coat of claim 5 wherein the maximum carbon chain length is 31.

7. A manufactured seed comprising:
a unit of totipotent plant tissue, and
a containing portion enclosing the totipotent plant tissue, said containing portion comprising a substrate having a wax coating substantially encasing the substrate, said containing portion resisting cracking at temperatures below about 1° C. for at least four days, wherein the wax coating comprises paraffin and a wax composition, wherein a ratio of the wax composition to paraffin is from about 1:9 to about 9:1, and wherein the wax composition comprises about 50% by weight petroleum wax, about 20% by weight microcrystalline petroleum wax, about 20% by weight ethylene-vinyl acetate copolymer, and about 10% hydrocarbon resin.

8. The manufactured seed of claim 7 wherein said wax coating has a viscosity of about 23 centipoise to about 50 centipoise at a predetermined application temperature.

9. The manufactured seed of claim 7 wherein said wax coating has a melting point of at least 49° C.

10. The manufactured seed of claim 7 wherein said substrate is formed from cellulose.

11. The manufactured seed of claim 7 wherein said containing portion is water impermeable.

12. The manufactured seed of claim 7 wherein the paraffin hydrocarbon chains have a Gaussian distribution with a maximum carbon chain length within the range of about 28 to 33.

13. The manufactured seed of claim 12 wherein the maximum carbon chain length is 31.

14. A method of making a manufactured seed comprising:
providing a unit of a totipotent plant tissue;
enclosing said totipotent plant tissue within a seed coat having a containing portion, wherein said containing portion comprises a substrate having a wax coating, the wax coating substantially encasing the substrate, wherein said containing portion resists cracking at temperatures below about 1° C. for at least four days, wherein the wax coating comprises paraffin and a wax composition, wherein a ratio of the wax composition to paraffin is from about 1:9 to about 9:1, and wherein the wax composition comprises about 50% by weight petroleum wax, about 20% by weight microcrystalline petroleum wax, about 20% by weight ethylene-vinyl acetate copolymer, and about 10% hydrocarbon resin.

15. The method of claim 14 wherein said wax coating has a viscosity of about 23 centipoise to about 50 centipoise at a predetermined application temperature.

16. The method of claim 14 wherein said wax coating has a melting point of at least 49° C.

17. The method of claim 14 wherein said substrate is formed from cellulose.

18. The method of claim 14 wherein said manufactured seed coat is water impermeable.

19. The method of claim 14 wherein the paraffin hydrocarbon chains have a Gaussian distribution with a maximum carbon chain length within the range of about 28 to 33.

20. The method of claim 19 wherein the maximum carbon chain length is 31.

21. A manufactured seed comprising:
a unit of totipotent plant tissue, and
a containing portion enclosing the totipotent plant tissue, said containing portion comprising a substrate having a wax coating, said containing portion resisting cracking at temperatures below about 1° C., wherein the wax coating comprises paraffin and a wax composition, wherein a ratio of the wax composition to paraffin is from about 1:9 to about 9:1, and wherein the wax composition comprises about 50% by weight petroleum wax, about 20% by weight microcrystalline petroleum wax, about 20% by weight ethylene-vinyl acetate copolymer, and about 10% hydrocarbon resin.

22. A seed coat for manufactured seeds comprising a substrate having a wax coating and wherein the seed coat resists cracking at temperatures below about 1° C., wherein the wax coating comprises paraffin and a wax composition, wherein a ratio of the wax composition to paraffin is from about 1:9 to about 9:1, and wherein the wax composition comprises about 50% by weight petroleum wax, about 20% by weight microcrystalline petroleum wax, about 20% by weight ethylene-vinyl acetate copolymer, and about 10% hydrocarbon resin.

23. A method of making a manufactured seed comprising:
providing a unit of a totipotent plant tissue;
enclosing said totipotent plant tissue within a seed coat having a containing portion, wherein said containing portion comprises a substrate having a wax coating wherein said containing portion resists cracking at temperatures below about 1° C., wherein the wax coating comprises paraffin and a wax composition, wherein a ratio of the wax composition to paraffin is from about 1:9 to about 9:1, and wherein the wax composition comprises about 50% by weight petroleum wax, about 20% by weight microcrystalline petroleum wax, about 20% by weight ethylene-vinyl acetate copolymer, and about 10% hydrocarbon resin.

* * * * *